US00PP09538P

United States Patent [19]

Christensen

[11] Patent Number: Plant 9,538

[45] Date of Patent: May 7, 1996

[54] HYBRID TEA ROSE PLANT 'JACLAF'

[75] Inventor: Jack E. Christensen, Ontario, Calif.

[73] Assignee: Bear Creek Gardens, Inc., Medford, Oreg.

[21] Appl. No.: 413,463

[22] Filed: Mar. 28, 1995

[51] Int. Cl.[6] ..... A01H 5/00

[52] U.S. Cl. ..... Plt./11

[58] Field of Search ..... Plt./11, 19, 18

*Primary Examiner*—Howard J. Locker

*Attorney, Agent, or Firm*—Klarquist Sparkman Campbell Leigh & Whinston

[57] ABSTRACT

A rose plant of the Hybrid Tea class, characterized by the unique combination of its attractive lavender-colored flowers, its strong fragrance, its dark green, glossy foliage, its resistance to disease, and its vigorous, upright habit of growth.

1 Drawing Sheet

The present invention relates to a new and distinct variety of rose plant of the Hybrid Tea class which was originated by me by crossing the variety AROlical, U.S. Plant Pat. No. 6,000, with an unnamed seedling.

The primary objective of this breeding was to produce a new rose variety having lavender-colored flowers, the fragrance and dark foliage of the female parent combined with the vigor, shiny, glossy foliage, and health of the male parent. This objective was substantially achieved, along with other desirable improvements, as evidenced by the following unique combination of characteristics that are outstanding in the new variety and that distinguish it from its parents, as well as from all other varieties of which I am aware:

1. Heavy, strong fragrance;
2. Dark green, glossy foliage;
3. Lavender hybrid tea flowers;
4. Vigorous, upright growth; and
5. Good resistance to disease.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—AROlical, U.S. Plant Pat. No. 6,000.

*Pollen parent.*—Unnamed seedling.

Classification:

*Botanical.*—Rosa hybrida.

*Commercial.*—Hybrid Tea.

FLOWER

Observations made from specimens grown in a garden environment at Somis, Calif., in April through October, 1994.

Blooming habit: Recurrent.

Bud:

*Size.*—1½ inches to 2 inches long when the petals start to unfurl.

*Form.*—The bud form is long, pointed ovoid.

*Color.*—When sepals first divide, bud color is Greyed-Purple Group 185A. When half blown, the upper and lower sides of the petals are Greyed-Purple Group 185D.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 137D. Shape: Funnel. Size: Small (¼ inch by ¼ inch). Surface: Smooth.

*Peduncle.*—Length: Medium (3 inches to 3½ inches). Surface: Smooth. Color: Medium green. Strength: Stiff, erect.

Bloom:

*Size.*—Large. Average open size is 5 inches to 5½ inches.

*Borne.*—Singly.

*Stems.*—Medium, strong. Average length is about 18 inches to 20 inches.

*Form.*—When first open: Retains its form to the end, outer petals curl back.

*Petalage.*—Number of petals under normal conditions: 25.

*Color.*—The upper side of the petals is Greyed-Purple Group 185D. The reverse side of the petals is Greyed-Purple Group 185D. The base of each petal has a Whitish-Green (Green White Group 157C to D, ⅜ inch by ⅜ inch) half moon at the point of attachment. The major color on the upper side is Greyed-Purple Group 185D.

*Variegations.*—Occasional whitish streak on the guard petals.

*Discoloration.*—The general tonality at the end of the first day: No change. At the end of the third day: No change.

*Fragrance.*—Strong.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Long (6 to 7 days). As a cut flower: Not tested.

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.
*Styles.*—Color: Yellow.
*Stigmas.*—Color: Greenish white.

Form: Bush.

Growth: Vigorous, upright, branching. Mature plant height in Somis, Calif. is 5 feet high by 4 feet wide.

Foliage:
*Number of leaflets on normal mid-stem leaves.*—5 or 7.
*Size.*—Large (6 inches by 4½ inches).
*Quantity.*—Abundant.
*Color.*—New foliage: Greyed-Purple 183A. Old foliage: Upper Surface: Green Group 139A. Lower Surface: Green Group 139B.

Leaflets:
*Shape.*—Pointed oval.
*Texture.*—Upper side: Leathery, glossy.
*Edge.*—Serrated.
*Serration.*—Single, small.
*Petiole rachis.*—Color: Green.
*Petiole underside.*—Smooth.
*Stipules.*—Medium (¾ inch), bearded.
*Disease resistance.*—Resistant to mildew and rust under normal growing conditions at Somis, Calif.

Wood:
*New wood.*—Color: Reddish green. Bark: Smooth.
*Old wood.*—Color: Green. Bark: Smooth.

Prickles:
*Quantity.*—On main canes from base: Ordinary. On laterals from main canes: Ordinary.
*Form.*—Medium (⅜ inch to ½ inch), hooked downward.
*Color when young.*—Red.

Small prickles:
*Quantity.*—On main stalks: None. On laterals: None.

I claim:

1. A new and distinct variety of rose plant of the Hybrid Tea class, substantially as herein shown and described, characterized particularly as to novelty by the unique combination of its attractive lavender-colored flowers, its strong fragrance, its dark green, glossy foliage, its resistance to disease, and its vigorous, upright habit of growth.

* * * * *

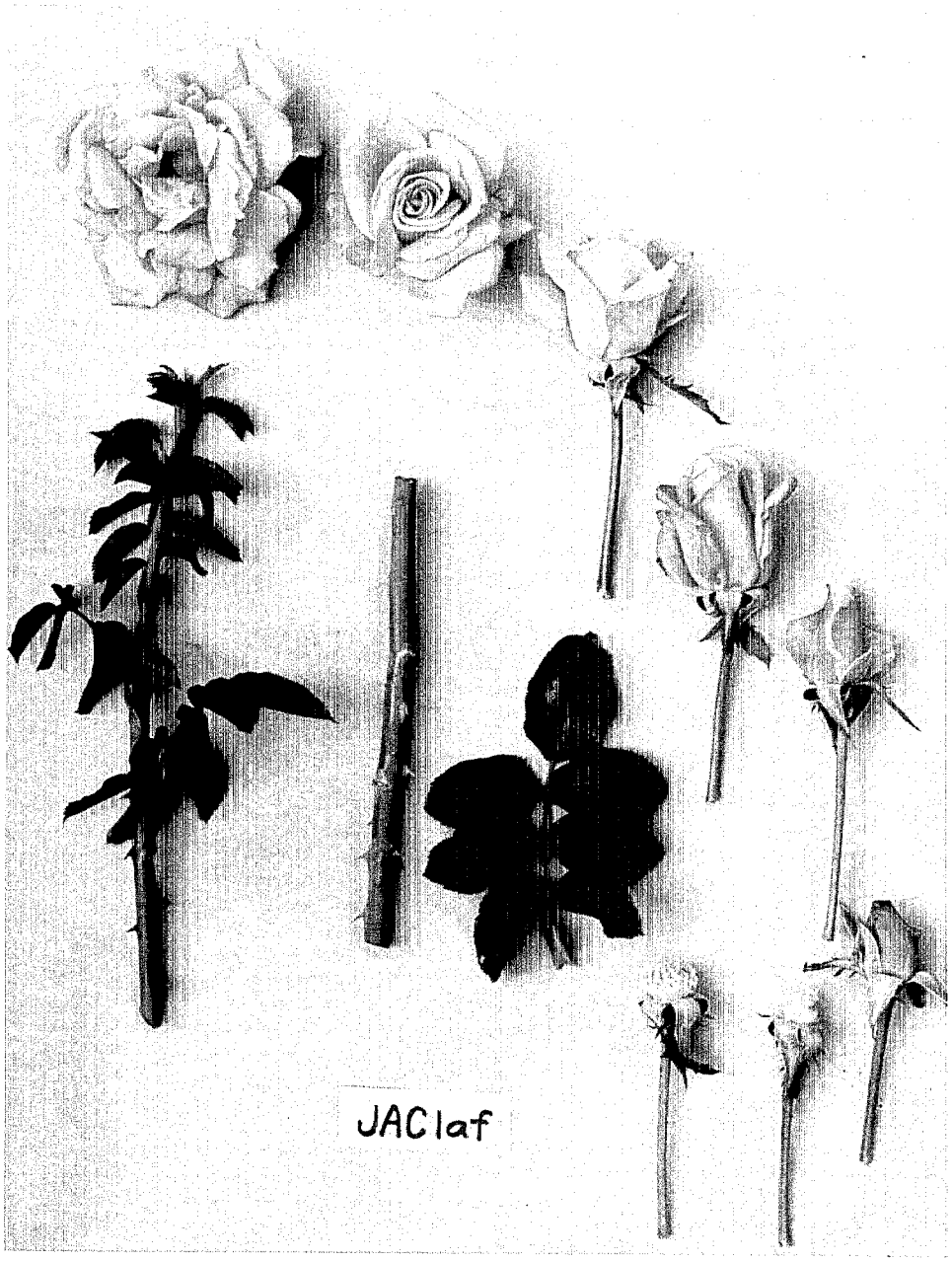
JACIaf

UNITED STATES PATENT AND TRADEMARK OFFICE

CERTIFICATE OF CORRECTION

PATENT NO. : PP 9,538

DATED : May 7, 1996

INVENTOR(S) : Jack E. Christensen

It is certified that error appears in the above-indentified patent and that said Letters Patent is hereby corrected as shown below:

Column 2, line 21, "open: Retains its form" should read --open: High centered. Permanence: Retains its form--.

Signed and Sealed this

Eighth Day of October, 1996

*Attest:*

*Attesting Officer*

BRUCE LEHMAN

*Commissioner of Patents and Trademarks*